United States Patent [19]

Shirakawa et al.

[11] Patent Number: 5,663,262

[45] Date of Patent: Sep. 2, 1997

[54] COMPOUND CONTAINING AN OXAMIC ACID GROUP, A PROCESS FOR PRODUCING THE COMPOUND, AND A RESIN COMPOSITION CONTAINING THE COMPOUND

[75] Inventors: Shinsuke Shirakawa; Kazunori Kanda; Mitsuo Yamada, all of Osaka; Kei Aoki, Nara; Satoshi Urano, Kyoto; Nobuaki Tomita, Nara, all of Japan

[73] Assignee: Nippon Paint Co., Ltd., Osaka, Japan

[21] Appl. No.: 433,097

[22] Filed: Nov. 8, 1989

[30] Foreign Application Priority Data

Nov. 11, 1988 [JP] Japan .................................. 63-286308

[51] Int. Cl.[6] .......................... C08F 26/00; C08F 126/00; C08F 226/00; C07C 69/52
[52] U.S. Cl. .......................... 526/312; 525/217; 525/218; 525/220; 526/311; 560/221; 560/222; 560/224; 562/448; 562/450; 562/455
[58] Field of Search .................................. 526/311, 312; 525/217, 218, 220; 560/221, 222, 224; 562/448, 450, 455

[56] References Cited

U.S. PATENT DOCUMENTS 4,684,710  8/1987  Schimmel et al. ....................... 528/26

OTHER PUBLICATIONS

Diefenbach et al., "Unsaturated Derivatives of Urea and Oxalic Acid", Makromolekular Chemie 1970, 131, pp. 247–257 (German).

Chemical Abstracts vol. 72, 1970, 100246q (Makromol. Chem. 1970, 131, 247–47).

*Primary Examiner*—Paul R. Michl
*Assistant Examiner*—P. Niland
*Attorney, Agent, or Firm*—Armstrong, Westerman, Hattori, McLeland & Naughton

[57] ABSTRACT

The present invention relates to compounds containing an oxamic acid group, which show high reactivity and have stability for water and are used as paints, adhesives, and plastic materials etc. in the form of a reaction material or a resin. Since into these compounds an oxamic acid group is introduced in a part of the molecule and the oxamic acid group is an ionic functional group, the compounds show superior solubility and dispersing character in water and also, since the oxamic acid group is a group of a disappearing type with heating, the compounds do not remain, after hardening, in the hardened product. Accordingly, the hardened products obtained from these compounds are superior in water-resistant and anticorrosion properties and in durability.

15 Claims, No Drawings

COMPOUND CONTAINING AN OXAMIC ACID GROUP, A PROCESS FOR PRODUCING THE COMPOUND, AND A RESIN COMPOSITION CONTAINING THE COMPOUND

BACKGROUND OF THE INVENTION

The present invention relates to a compound containing an oxamic acid group which has both the properties of high reactivity and high stability for water and, in particular, to a compound containing an oxamic acid group which is, as a material having a new function, usable as paints, adhesive agents, plastic materials, and the like in a form of reaction material or resin, in addition, to a process for producing the compound, and to a resin composition containing the compound.

In a case of that coating by a resin in an organic system is carried out in a water medium, it is required to lower viscosity of a solution of the resin to facilitate coating by a physical method and thus, a technique to dissolve or disperse the resin in an organic system becomes important.

The dissolving and/or dispersing of the resin in an organic system are possible by a quality improvement (character change) of the resin with introduction of a hydrophilic group and/or an ionic functional group in a part of the resin molecule and/or by dispersion of the resin with use of a surface active substance having a hydrophilic and/or an ionic functional group, but there has been widely used a method where the ionic functional group is introduced in a part of the resin.

This ionic functional group contributes for dispersion and stabilization of the resin into water in a stage of that the resin is in a paint condition, as described above, and then in a process of coating followed by resin-hardening, sometimes displays a function of an acid catalyst for hardening and, furthermore, can give a crosslinking structure by reacting with a functional group of other hardening agents. However, the functional group remaining in a hardened paint film causes lowering in water-resisting and anticorrosion properties and in durability of the paint film.

If an example is cited, in an anionic resin for electrodeposition, while an ionic functional group such as a carboxyl group shows an anionic character and contributes for stabilization of a resin-dispersing solution, it contributes for separating resin on a plate by being neutralized on turning of an electric current. However, in a stage of a paint film having been hardened with heating, the remainder of said carboxyl group etc. lowers anticorrosion and water-resisting properties of the paint film. Furthermore, a carboxyl group etc. remaining during a hardening time, since it has an anionic character, may lower reactivity of the agent in a case of that a hardening agent such as an isocyanate etc. is used.

SUMMARY OF THE INVENTION

Under these situations, it is at present wanted to get a functional group which remains as an ionic group in a paint (a solution) condition, but after transforming into a film or a paint film losts the ionic character. More desirable is a functional group of the ionic character if it acts as an ionic group as itself or by neutralization with an alkali, but loses the ionic character by thermal decomposition with heating during a process of conversion into a paint film, that is, if it is an ionic group of an ion-disappearing type.

Accordingly, the first object of the present invention is to provide a high molecular weight compound which, is stable in water, has a functional group being disappeared with heating, shows superiority in such properties as affinity and mutual solubility with other organic compounds and resins and as solubility for solvents, and may be used as a composition.

The second object of this invention is to provide a low molecular weight compound which has a functional group of ionic character being disappeared with heating and is able to favorably use for synthesis of said high molecular weight compound.

The third object of this invention is to provide a composition being transformed into a material of hardening character or a paint by using said high molecular weight compound as a component.

The present inventors looked for an ionic functional group disappearing with heat, to achieve these objects.

Hitherto, as a functional group which varies character with heating and undergo decarboxylation, for example, is known the following ethoxalylamide (refer to Japanese Official Patent Provisional Publication, showa 63-45246, and Japanese Official Patent Provisional Publication, showa 63-46209), —CONHCOCOOR(R=a hydrocarbon group)

but this functional group shows poor stability for water and is easily hydrolyzed, even if a small amount of water is added, transforming it into an amide group (—$CONH_2$), so that it can not be a stable ionic group as itself.

Also, the compounds having an oxamic acid ester group analogous to the above have been reported in U.S. Pat. No. 4,846,710

—NHCOCOOR(R=a hydrocarbon group)

as a hardening agent for compounds containing an amino group, but this functional group itself is not an ionic functional group.

On the other hand, the following oxamic acid group is

—NHCOCOOH a stable functional group, and it disappears causing decarboxylation with heating.

On a basis of knowledge of this kind, the present inventors attempted to introduce an oxamic acid group in a part of a high molecular weight compound. Hereinafter, this high molecular weight compound is called a resin modified with oxamic acid. Furthermore, the inventors attempted to introduce an oxamic acid group into a part of a low molecular weight compound in order to get profitably a high molecular weight compound of the above kind and, in addition, to invent a production process to get a low molecular weight compound of this kind with facility. Hereinafter, the low molecular weight compound is called a monomer containing an oxamic acid group.

The monomer containing an oxamic acid group and the oxamic acid group in a resin molecule modified with oxamic acid, relating to the present invention, show strong acidity of a proton-releasing type in an aqueous solution and are a functional group of high stability for water. Therefore, the monomer containing an oxamic acid group and the resin modified with oxamic acid relating to this invention and containing one or more of the oxamic acid group in the molecule are needless to say soluble in organic solvents and also dispersion and disolution in water are possible with forming salts by an alkali neutralization, although there is a case insoluble by themselves. For example, a salt with amines (shown as $NR_3$) is as follows.

Also, as described above, since the oxamic acid group is strongly acidic and has an active hydrogen atom in the carboxylic acid moiety, the group is nucleophilic in reaction, so that easily reacts with an electrophilic functional group with heating and so on. For example, with an epoxy group takes place an addition reaction as follows.

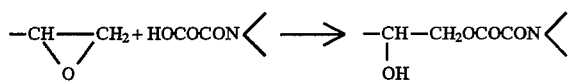

Furthermore, the oxamic acid group shows high reactivity an active hydrogen atom and, for example, undergoes condensation reaction with an amino group (H—N≦) as follows.

Like this, the monomer containing an oxamic acid group and the resin modified with oxamic acid relating to this invention have both kinds of reactivity with an electrophilic compound and/or resin, and an active hydrogen-containing compound and/or resin and, therefore, they have various kinds of utility as a crosslinking or hardening agent with a use of such reactivities. Particularly, an use for resin-hardening is mentioned due to high reactivity of the oxamic acid group.

Besides, since the monomer containing an oxamic acid group relating to the invention involves a group of radical polymerization character in the molecule and, due to this group, radical polymerization is possible, for example, by performing homopolymerization as the need arises or by performing copolymerization with other monomers of addition polymerization character, converting it into a high molecular weight compound, and furthermore, by introducing a resin residue, it is possible to afford an ability to form a film.

The oxamic acid group also has properties of decomposition and disappearance. As described below, it converts into a formamide group by decarboxylation at low temperature (with heating for 0.5~ a few hours at about 150°~200° C.), which has been confirmed by acid value (AV), IR, and NMR, and also, into a nitril group by decarboxylation, decarbonylation, and dehydrogenation at high temperature (with heating for a few seconds at 300° C. or higher), which has been confirmed by PGC-MS (gas chromatography with thermal decomposition and mass spectrum).

at low temperature:—NHCOCOOH→—NHCHO at high temperature:—CH₂NHCOCOOH→—C≡N

Accordingly, in a case of that the resin modified with oxamic acid relating to the invention is used as a coating material, can be given a paint film of a high degree in properties such as water-resistant and alkali-resistant properties. Similarly, due to a property of thermal decomposition, the monomer containing an oxamic acid group and the resin modified with oxamic acid can be used as an acid catalyst not lowering water-resistant and anticorrosion properties.

Hereinafter, the present invention is explained in detail.

At first, the monomer containing an oxamic acid group is represented by the following general formula.

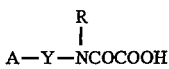

[in the formula, A represents a group of radical polymerization character; Y represents an alkylene group of carbon number 1~8, but the carbon atom can be, in part, replaceable with oxygen atom; and R represents a hydrogen atom, an alkyl group of carbon atom 1~5, or a benzyl group, but be able to have a hydroxyl group.]

Although a group of radical polymerization character A is not especially limited, for example, the following groups are cited.

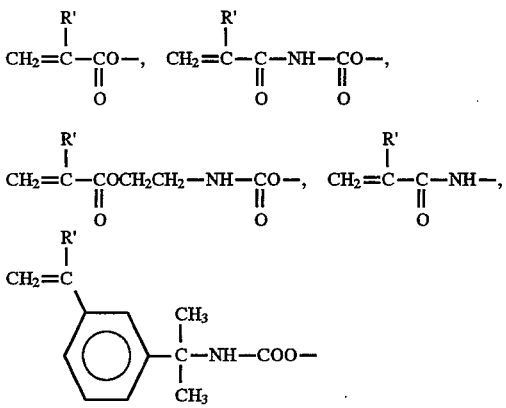

[here, R' represents a hydrogen atom or a methyl group.]

As seen above, in the monomer containing an oxamic acid group in this invention the organic group Y combining a group of radical polymerization character A with an oxamic acid group should be the one having carbon number of more than one. Although there has been reported a compound containing an oxamic acid group in a literature, Makromolekular Chemie 1970, 131, pp. 247~257,

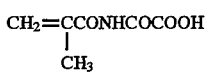

this compound has not the above-mentioned organic group Y and solubility for organic solvents is very poor.

Although said monomer containing an oxamic acid is useful for other purposes besides the use for synthesis of the resin modified with oxamic acid in this invention, if the molecular weight of monomers containing an oxamic acid group is too small or too large, in a case of that the monomers containing an oxamic acid group are mixed with an optional composition as an acid catalyst or a hardening agent, the mutual solubility and affinity with other organic compounds and resins become poor and the stability and dispersing character in the composition also become poor and, as a result, various kinds of addition effects expectable as an acid catalyst and as a hardening agent for the oxamic acid group are not displayed. Not only this problem, but also other problems are affraid in a practical use.

Although the synthetic method for the monomers containing said oxamic acid group is not especially limited, one example is to use that a reaction between an amino group and an oxalic acid ester gives an oxamic acid ester which is hydrolyzed yielding an oxamic acid group and, in this case, a synthesis is treatment of an amino compound having a group of radical polymerization character with an equivalent mole or an excess of an oxalic acid ester such dimethyl oxalate and diethyl oxalate followed by hydrolysis of the produced ester.

Here, as the amino compounds having a group of radical polymerization character are exemplified, for example, polymerizable amines such as N-(6-aminohexyl) methacrylamide etc., but there is no limitation with this compound.

The conditions for the reaction between said amino compound and an oxalic acid ester are not especially limited, but proper setting is preferred depending upon the kind of starting material etc. For example, an amino compound diluted with an optional solvent is added dropwise maintaining reaction temperature at 20°~30° C. during 1.5~3 hours into a definite amount of diethyl oxalate and then, further stirring of the obtained mixture is recommended to proceed the reaction. In this case, if the reaction temperature is too high or the reaction progress is too fast, it is afraid that two moles of the amine react with one mole of diethyl oxalate, so a high molecular weight compound may be produced. Besides, as a diluting agent are cited a low class of alcohols such as ethanol and isopropanol etc., aromatic hydrocarbons such as benzene and xylene etc., aliphatic hydrocarbons such as hexane and pentane etc., and ethers such as diethyl ether and tetrahydrofuran etc.

Hydrolysis of the obtained oxamic acid esters, for example, can be carried out at 20°~30° C. with adding a necessary amount of water and by using an amine (triethylamine etc.) as a catalyst. In this case also, if the reaction temperature is too high, an amine isolated with hydrolysis reacts with another oxamic acid ester or an oxamic acid salt and, for example, forms a bond >NCO—CON<, which may lead to a high molecular weight compound.

Alcohols forming during reaction and excess amines may be removed by heating under reduced pressure etc. also, when hydrolysis is carried out with addition of a large amount of water, the aimed monomer containing an oxamic acid group is obtained in a form being dissolved and dispersed in water as an ammonium salt, but if neutralized by an acid, it can be taken as crystals insoluble in water. It was confirmed by NMR and IR that the hydrolysis from the oxamic acid ester into the forementioned oxamic acid has taken place in the C—O bond, and its reaction yield in percentage is 80% or more.

The below-described ① shows an example for the forementioned synthesis, in which at first methacrylamide is obtained and this amide treated with an oxalic acid ester leading to an ester compound that is hydrolyzed.

However, the synthesis of a monomer containing an oxamic acid group is not limited with this example and also, the below-described methods such as such as ②~④ can be applied.

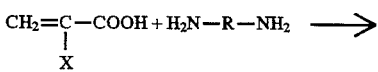

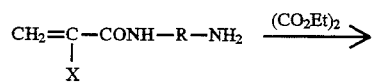

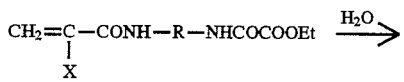

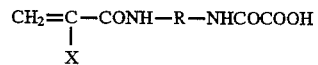

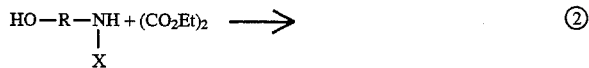

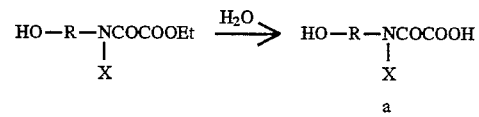

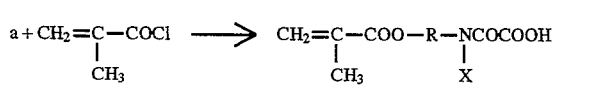

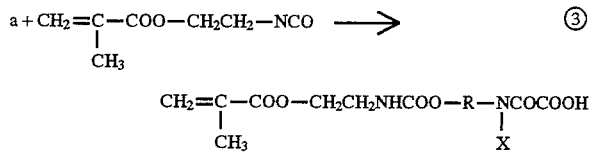

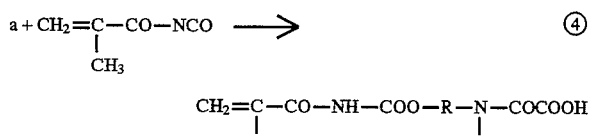

[in the formulas, X represents hydrogen, halogen, or a monovalent hydrocarbon group substituted with a functional group or unsubstituted, etc.; R represents a hydrocarbon group substituted with a functional group or unsubstituted, etc.]

Hereinafter, novel examples of the monomers containing an oxamic acid group relating to this invention are explained. That is, in said monomers containing an oxamic acid group, is explained a monomer containing an oxamic acid group, in which at least one 1-substituted (unsubstituted)-2-hydroxyethyl group is combined with a nitrogen atom of at least one oxamic acid group. Since the monomer

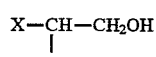

[X represents hydrogen, halogen, a hydrocarbon substituted with a functional group or unsubstituted, and an optional functional group etc.] containing an oxamic acid group has a hydroxyl group besides the oxamic acid group, the reactivity is better and, as a result, for example, a paint film of improved crosslinking density and stronger hardness can be obtained.

Said monomers containing an oxamic acid group can be prepared by adding a necessary amount of water to a morpholine-2,3-dione group substituted with a proper organic group having the below-described ethylenic unsaturated bond:

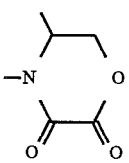

and then, by performing hydrolysis under presence of an amino compound to open the morpholine group.

Here, said morpholinedione can be prepared, for example, from a reaction of the below-described N-hydroxyethylmorpholinedione:

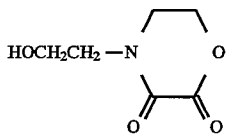

with a compound having a polymerizable unsaturated bond. Besides, the morpholinedione is obtained from a reaction of diethyl oxalate with diethanolamine. Although the compound having a polymerizable unsaturated bond is not especially limited, are cited, for example, acryloyl chloride, methacryloyl chloride, isocyanatoethyl methacrylate, methacryloyl isocyanate, methyl methacrylate, ethyl methacrylate, ethyl acrylate, butyl acrylate, m-isopropenyl-α, α-dimethylbenzyl isocyanate.

Hydrolysis of the obtained morpholinedione substituted with an organic group and ring cleavage of the morpholinedione can be carried out in the same way as for hydrolysis of said oxamic acid ester. By the way, regarding the ring cleavage reaction of substituted morpholinediones, there has been reported in U.S. Pat. No. 4,118,422 a synthesis of polyols by a reaction of said morpholine with polyoxypropylamine having a primary amine.

Resins modified with oxamic acid are explained. These are compounds containing an oxamic acid group shown by the below general formula (II).

$$P \!-\!\!\left(\!\!\begin{array}{c} R \\ | \\ NCOCOOH \end{array}\!\!\right)_{\!n} \tag{II}$$

[in the formula (II), P represents a polymer residue having a molecular weight of 1000 or more, R represents a hydrogen atom, an alkyl group of carbon atom 1~5, or a benzyl group, and n represents a positive integral number. But R may have a hydroxyl group as a substituent.]

That is, the resins modified with oxamic acid are those chemically modified with an oxamic acid group by introducing one or more of an oxamic acid group into an optional position in a main or a side chain of resins such as acryl resin, polyester resin, polyamide resin, epoxy resin, amino resin, polyethylenimine resin, hydrocarbon resin, silicone resin, fluororesin, and their modified resins etc., and the bonding position and the bonding number are not limited. Concretely, the introducing position and number of the oxamic acid group can be optionally combined each other, for example, at an end position of the main chain and both ends, a specified position in a midway of the main chain or an unspecified position, an end position of the side chain, and a specified position in a midway of the side chain or an unspecified position.

For said acryl resin are cited, as good examples, the copolymers between an optional polymerizable monomers and a monomer in an acryl series containing a hydroxy group or a monomer in acryl series containing an epoxy group. As the former polymerizable monomers are cited optional acrylic acid esters such as methyl acrylate, ethyl acrylate, and n-butyl acrylate etc.; methacryl acid esters such as methyl methacrylate, ethyl methacrylate, and n-butyl methacrylate etc.; acid or amide monomers in an acryl series such as acrylic, methacrylic, and itaconic acids, and acrylamide and diacetoneacrylamide etc.; optional monomers such as styrene and vinylstyrene etc. As the latter monomers in a hydroxyl group-containing acryl series are cited 2-hydroxyethyl acrylate and 2-hydroxyethyl methacrylate etc., and as the monomers in an epoxy group-containing acryl series are cited glycidyl methacrylate etc. The hydroxy and epoxy groups etc. in said resins can be used for introduction of an oxamic acid group. It is proper that the hydroxy group values of these resins are in a range of 5~100, and the acid values in a range of 2~150, and the molecular weight in a range of 1,000~1,000,000, but the values are not limited within the ranges.

As said polyester resins can be used the resins obtained from thermal polymerization condensation of polyvalents carboxyl acids represented by, for example, 2-valent carboxyl acids such as phthalic anhydride, isophthalic acid, terephthalic acid, succinic anhydride, adipic acid, azelaic acid, hexahydrophthalic anhydride, maleic anhydride, and fumaric acid etc., or 3-valent or 4-valent carboxyl acids such as trimellitic anhydride and pyromellitic anhydride etc. with polyalcohols such as ethyleneglycohol, propyleneglycohol, 1,6-hexanediol, diethyleneglycohol, triethyleneglycohol, glycerol, trimethylolpropane, pentaerythritol, and dipentaerythrite etc. The hydroxyl and carboxyl groups can be used for introduction of an oxamic acid group. Besides, favorable is that these have a hydroxyl value in a range of 5~150, an acid value in a range of 5~150, and a molecular weight in a range of 1,000~100,000, but that is not specially limited within the values.

As examples for polyamide resins are given compounds represented by the following formula:

[in the formula, $R^1$ and $R^2$ independently represent an alkylene, alkenylene, alkynylene, cycloalkylene, or arylene group of 1~20 carbon atoms substituted with a functional group or unsubstituted, and n is positive integral number of 2 or more.] As a commercially available product is favored 'Normex' produced from DuPONT Co. The amino group in the resins can be used for introduction of an oxamic acid group. Also, the molecular weight is preferred to be in a range of 200~100,000, but there is no problem even if it is deviated from the range.

As epoxy resins are favored the resins containing an epoxy group in a main and/or side chains and having epoxy equivalents of 180~10,000. For examples, are cited an epoxy resin of an epibis type, an epoxy resin of a novolac type, an epoxy resin of a resorcinol type, an epoxy resin of a polyglycohol type (a glycohol ether type), and an epoxy resin of a cyclic oxirane type, all of which can be obtained from bisphenol A and epichlorohydrin. Introduction of an oxamic acid group is carried out by being derived from the epoxy group in these resins.

As amino resins are favorably used the etherized amino resin etc. which are obtained with addition condensation of melamine, guanamine, urea, and these derivatives etc. with formaldehyde followed by modification with alcohol. More concretely, are cited, as good examples, methylated melamine resin, butylated melamine resin, methylated and butylated melamine resins, and benzoguanamine resin etc. As commercially available products are preferred a melamine resin J-820-60 (molecular weight of 1240 averaged by number) made by Dainippon Inki Kagaku Kogyo Co., a melamine resin J-830-60 (molecular weight of 1120 averaged by number) made by the same company and a guanamine resin BL-60 (acid value of 0.5 or less) and BX-3900 (acid value of 0.5 or less), both of which are made by Sanwa Chemical Co. The imino and methylol groups in these resins can be used for introduction of an oxamic group.

Also, the molecular weight is not especially limited, but a preferred range is in 200~100,000.

As polyethyleneimine resins are, for example, the compounds shown by the following general formula,

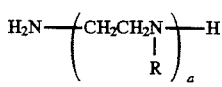

[in the formula, R=

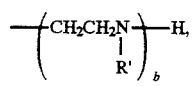

a=1~100, and b=1~100] and so on can be used and, furthermore, compounds are preferred, for which the amine values of a primary amine and a secondary amine are 5 or more and the molecular weight is in a range of 600~100,000. As commercially available products are exemplified Epomine SP-103 (molecular weight of 250), Epomine SP-200 (molecular weight of 10,000), Epomine P-1000 (molecular weight of 70,000), and Epomine SP-018 (molecular weight of 1,800), all of which were made from Nippon Shokubai Kagaku Kogyo Co.

As silicone resins are favorable used the silicone resins, as shown with the following formula, having an amino group at both (or one) end positions:

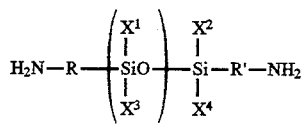

[in the formula, R and R' independently represent an alkylene, alkenylene, alkynylene, cycloalkylene, or arylene group substituted by a functional group of carbon number 1~20 or unsubstituted, and $X^1$~$X^4$ independently represent hydrogen, or an aryloxy, an alkoxy group of carbon number 1~20, or an aryl, or an ester bond or an urethane bond, or an alkyl group of carbon number 1~400 which is able to involve a carboxylic acid group, and n represents a positive integral number of 2 or more. Here, the end amino group can be used for introduction of an oxamic acid group. The molecular weight is preferred to be in a range of 200~500,000.

As hydrocarbon resins are exemplified the resins in a butadiene series. As the butadiene resins are preferable for use the polybutadienes of a 1,4 type or 1,2 type (the contents of each structure are optional), and it is recommended that at least an end functional group is a hydroxyl, an epoxy, an amino, and an isocyanate (—NCO) group etc. As commercially available products can be used, for example, a polybutadiene having a hydroxyl group at an end position R-45 EPI and a polybutadiene having a NCO group at the end position HTP-5MLD, both of which are made from Idemitsu Sekiyu Kagaku Co. Also, the molecular weight is preferred to be in a range of 150~50,000, but it is not limited in the range.

As fluororesins are favorably used the copolymer etc. of fluorinated modified resins such as a fluorinated acrylic acid esters and fluorinated methacrylic acid esters (for examples, 2,2,2-trifluoroethyl acrylate, 1,1,1,3,3,3-hexafluoroisopropyl acrylate, and 2,2,2-trifluoroethyl methacrylate etc.) or fluorinated styrene (for an example, 2,3,4,5,6-pentafluorostyrene etc.) with an acrylic acid or an methacrylic acid ester monomer containing a hydroxyl or an epoxy group. The hydroxyl or epoxy group can be used for introduction of an oxamic acid group. Also, the ratio of said fluorinated modified monomer against other monomers in an acryl series is 1~99/99~1 and the molecular weight is preferred to be in a range of 500~1,000,000.

The acid value of these oxamic acid-modified resins is wanted to be 2 or more from a point of affinity for water. More concretely, it is preferred that the acid value is about 5~500 and most preferred to be about 5~150. As the acid value increases, the solubility for water or dispersion ability in water increase, so that it becomes possible to use those as water-soluble coating resin or coating resin for electrodeposition.

Using the resin residue having a functional group (—OH, —COOH, and —NH$_2$ etc.) to introduce an oxamic acid group as mentioned above, a resin modified with oxamic acid can be synthesized by introducing an oxamic acid group as described below.

At first, if the functional group to introduce an oxamic acid group is an amino group, the modification can be carried out by that the functional group itself is allowed to react with an oxalic acid ester and then, the oxamic acid ester part is hydrolyzed. If said functional group is a hydroxyl group or a carboxyl group, the oxamic acid group can be introduced by that a compound half-blocked by a monooxalic acid ester, which is obtained by treating a reaction product between hydroxylamine and diethyloxalic acid with diisocyanate, is subjected to react with said functional group in the resin. For example, for a hydroxyl group in an optional resin, the reaction is shown as follows.

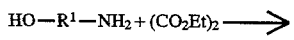

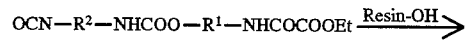

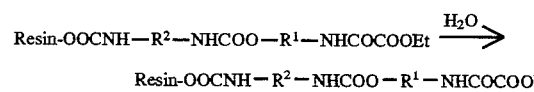

[in the formulas, $R^1$ and $R^2$ independently represent an alkylene group of carbon number 1 to 20, an alkenylene, an alkynylene, a cycloalkylene, or an arylene group.]

Furthermore, for a glycidyl group in a resin an amination carried out by using a ketimine etc. and then, an oxamic acid group can be introduced. Hereinafter, taking an epoxyresin (Ep) as an example, one example for the synthetic process is shown with chemical reaction formulas (only an end position or a part of the resin is in detail shown here).

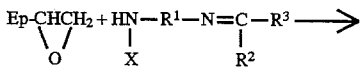

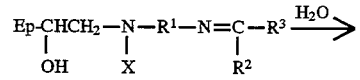

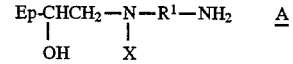

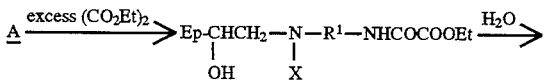

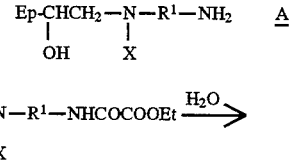

-continued $$\text{Ep-CHCH}_2\underset{\underset{\text{OH}}{|}}{-}\text{N}\underset{\underset{\text{X}}{|}}{-}\text{R}^1\text{—NHCOCOOH}$$

[in the formulas, X is the same as above, and $R^1$, $R^2$, and $R^3$ independently represent a hydrocarbon group etc. substituted with a functional group or unsubstituted.]

Also, if said amino-modified epoxy resin $\underline{A}$ is treated with an equivalent mole of diethyl oxalate, is obtained an epoxy resin modified with oxamic acid having a repeating unit, as shown below, on the way of the chain.

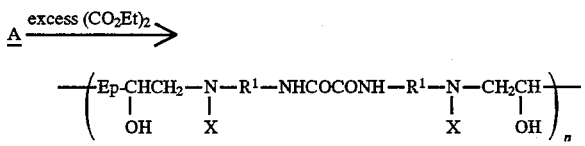

[in the formula, $R^1$, X and n are the same as above.]

Besides, the synthetic method for the resin modified with oxamic acid in this invention is not limited by the introduction of an oxamic acid group into the resin residue as mentioned above, and for example, a method is also adapted that in a monomer stage an introduction of the oxamic acid group is carried out to synthesize said oxamic acid monomer and then, this monomer alone or together with other polymerizable monomers (vinylic compound etc.) is polymerized. Concretely, in a case of an acryl resin modified with oxamic acid, are at first synthesized an acrylic acid or a methacrylic acid derivative (an oxamic acid monomer), and one kind or more of the derivatives is polymerized or copolymerized with a monomer in an acrylic acid series or methacrylic acid series not containing an oxamic acid group, leading to a synthesis of an acryl resin modified with oxamic acid. Also, a modified resin can be gotten by copolymerizing the oxamic acid monomer with a polymerizable monomer (butadiene and styrene etc.) other than the monomer in the acrylic acid series.

Furthermore, said resins modified with oxamic acid relating to this invention, like said novel monomer containing an oxamic acid monomer, may be the compounds containing at least one oxamic acid group combined with an 1-substituted or unsubstituted 2-hydroxyethyl group at the nitrogen atom. Since the resins modified with oxamic acid of this type have a hydroxyl group besides the oxamic acid group, can make a paint film of strong hardness.

Said resins modified with oxamic acid having an oxamic acid group substituted with a hydroxylethyl group can be synthesized by a method similar to that used for the monomer containing an oxamic acid group, that is, hydrolysis of a substituted morpholinedione containing intramolecularly a resin residue followed by ring cleavage of the morpholine-2,3-dione. Besides, said morpholinedione substituted with a resin residue can be obtained by chemical modification of the resin resulting from said morpholinedione substituted with an organic group and, for this, an optional reactive functional group, if necessary, is previously introduced into the morpholinedione substituted with an organic group and/or the resin.

For the forementioned monomers containing an oxamic acid group and the resins modified with oxamic acid, although various use can be considered with no special limitation, the below-described use can be considered by using several kinds of properties being involved in the oxamic acid group.

At first, since the oxamic acid has nucleophilic reactivity, it can be used as a hardening agent for a resin of electrophilic character and, on the other hand, from a point of high reactivity of the oxamic acid group with an active hydrogen, can be used as a hardening agent for a resin having an active hydrogen as represented by melamine resin etc. For use of those kinds, among said monomers containing an oxamic acid group and the resins modified with oxamic acid, the compounds containing intramolecularly two or more of the oxamic acid group are suitable and, a resin composition of a hardening type can be prepared by distributing for the above monomers or resins a proper hardening resin and, if necessary, an addition agent such as a diluting solvent, a filling agent, and a coloring agent etc. A paint film of strong hardness can be obtained by applying the composition for a surface of proper board material followed by hardening with heating.

Since any resin modified with an oxamic acid easily reacts with an active hydrogen, it can be used as a hardening resin at low temperature, where an active hydrogen-containing compound such as a kind of amine or a melamine resin is used as a hardening agent, and so it can be put to practical use as a resin for coating or a resin for paint. For example, by adding an organic solvent and/or water to a resin modified with oxamic acid in this invention and, if necessary, by adding a basic compound such as an amino compound or a compound capable of a reaction of a mutual type (crosslinking) and, if further necessary, by adding an optional additive for paint such as an organic or an inorganic sealing agent, a coloring agent (an organic, an inorganic, or a metal pigment or dye etc.), a viscosity-lowering agent, a leveling agent, an antifoaming agent, and a surface-adjusting agent etc., a resin composition for paint is prepared, from which a film of high hardness can be obtained in a similar way as described above. Besides, in that case a composition ratio between the resin modified with oxamic acid (x) and a compound capable of mutually reacting with x, is not especially limited, but $$x/y=30-100/70-0$$

the ratio shown by this equation is preferred.

A compound capable of mutually reacting with the resin modified with oxamic acid is, for example, what at least a group chosen from a hydroxyl, an amino, and an epoxy groups is involved in the molecule. Since the oxamic acid group has a property of facile decomposition and disappearance with heating, the resin modified with oxamic acid can be used as a water-resistant and alkali-resisting, water-soluble resin for paint. Furthermore, from a point of a superior water-dispersing and water-soluble character (for example, an amine salt of oxamic acid etc.), the resin modified with oxamic acid in this invention is very useful as a resin for water paint and electrodeposition paint.

Similarly, the resins modified with oxamic acid in this invention having superior dispersing and soluble characters in water can be used as a surface-active agent for an optional resin. For example, by combining the resin modified with oxamic acid with at least one or more kinds of an oxamic acid derivative combined with an organic acid chosen from acrylic resin, polyester resin, polyamide resin, epoxy resin, amino resin, polyethyleneimine resin, silicone resin, resin in a butadiene series, fluororesin, and their modified resin, is prepared a resin composition of high dispersing character.

Moreover, since the oxamic acid group shows a strong acidity by releasing a proton in a water, for example, the monomers containing an oxamic acid group and the resins modified with oxamic acid can be used as an acid catalyst for hardening of an appropriate resin. In this case, since the oxamic acid group disappears after hardening, for example, there needs not to worry about a remainder in a hardened paint film which causes lowering film capacity.

The forementioned are representative examples for use, and the use of the monomers containing an oxamic acid group and the resins modified with oxamic acid is not limited within the forementioned and, for example, needless to say, an use as an electrification-protecting agent is possible. Also, although an explanation was previously given for the hardening resin composition, which contains a resin having an active hydrogen or a resin of electrophilic character and contains a monomer having an oxamic acid group or a resin modified with oxamic acid in this invention having two or more oxamic acid groups in the molecule, the reactivity of the oxamic acid group with an active hydrogen or an electrophilic functional group does not limit combination of the above both. That is, it is not necessary that one hand is a monomer containing an oxamic acid group and the other hand is a resin and, for example, a paint film of strong hardness can be made by that an active hydrogen-containing compound, which is represented by a polyamine (diethylenetriamine), is allowed to react with a monomer containing an oxamic acid group in this invention having two or more oxamic acid groups in the molecule. For a reaction with an electrophilic compound containing intramolecularly an epoxy group etc. is the same.

Next, with respect to an identification method for oxamic acid derivatives in this invention, there are cited a structure analysis by instruments such as IR, NMR, and GC-MS; molecular weight measurements by GPC (gel permeation chromatography) and physical properties measurements such as, for example, solubility, SP value, viscosity, hydroxyl group value, and acid value etc.; and formation and disappearance of the oxamic acid group and identification of a resin residue and other functional groups can be carried out by performing qualitative and quantitative analysis in combination with the above.

Hereinafter, as a example, identification results of epoxy resin modified with oxamic acid by using $^{13}$C-NMR and IR are described. This modified resin was obtained by introducing an oxamic acid group into an epoxy resin material; the commercial name of YD-011 (YD-011, a commercially available epoxy resin of an epi-bis type having epoxy equivalents of 450 made by Touto Kasei Co.) as the below and had a structure form of triethylammonium salt derivative.

In a flask equipped with a stirrer, a thermometer, a nitrogen-inlet tube, and a reflux condenser were placed 90 g of an epoxy resin material, and then, added 60 g of methyl isobutyl ketone to get a solution, which was warmed up to 120° C. under nitrogen atmosphere and to which was added 52 g of a ketimine material obtained from a reaction of diethylenetriamine with methyl isobutyl ketone. The mixture was subjected to a reaction at 120° C. for 1.5 hours and, after the reaction finished, cooled to 25° C., and hydrolysis of the ketimine was carried out with addition of 5.8 g of water to obtain an epoxy resin modified by an amine. Next, the reaction solution containing an amine-modified epoxy resin obtained as the above was added dropwise during 1.5 hours maintaining the reaction temperature at 30° C. to 58 g (0.4 moles) of diethyloxalate placed in a flask equipped with a stirrer, a thermometer, a dropping funnel, and a reflux condenser flask. After the dropping finished, stirring was further continued for 1 hour at 25° C. and then, crystals separated were taken by filtration. Then, the thus-obtained reaction product and 300 ml of water were placed in a flask and a hydrolysis reaction was carried out by adding dropwise 23 g of triethylamine (0.22 moles) during 30 minutes to obtain triethylammonium salt of an epoxy resin modified with an oxamic acid.

Assignments of major chemical shifts, δ(ppm) in $^{13}$C-NMR, are 166.2 and 163.3 for C=O in an oxamic acid group; 158.3, 142. 7, 127.4, and 113.9 for a benzene ring in bisphenol A; 59.0 for CH$_2$O—, >CH—OH, 41.1 for —CH$_2$NH—; 30.8 for >C< in bisphenol A; and —14.1 for —CH$_3$ in bisphenol A.

Assignments of major IR absorption spectra (wave number, cm$^{-1}$) are 3400 for O—H stretching vibration in —COOH; 1660 for C=O stretching vibration in —COOH; 1630 for C=O stretching vibration in —NHCO—; 1600, 1510, and 1460 for C=C stretching vibration of a benzene ring in bisphenol A; and 1580 for —NH— deformation vibration.

Furthermore, hereinafter is shown identification results for the below-described ethylenedioxamic acid, HOCOCONHCH$_2$CH$_2$NHCOCOOH , by means of $^{13}$C-NMR and IR.

Assignments of major chemical shifts, δ(ppm) in $^{13}$C-NMR, are 162.0 and 159.6 for C=O in an oxamic acid group and 38.5 for —CH$_2$—.

Assignments of major IR absorption spectra (wave number, cm$^{-1}$) are 3200 for O—H stretching vibration in —COOH; 1760 for C=O stretching vibration in —COOH; 1680 for C=O stretching vibration in —NHCO—; and 1560 for —NH— deformation vibration.

Since the monomers containing an oxamic acid group and the resins modified with oxamic acid relating to this invention involve an oxamic acid group in the molecule, they show very high stability for water and strong acidity and can be dissolved or dispersed in water by forming a salt with an amine etc. The oxamic acid group responsible for this speciality easily disappears by heating and converts into a functional group of non-ionic character.

Also, said monomers containing an oxamic acid group and the resins modified with an oxamic acid have high reactivity for an active hydrogen and a functional group of electrophilic character and, in addition, if necessary, can contain a resin residue or a functional group which is able to lead to a high molecular weight compound.

Furthermore, said monomers containing an oxamic acid group and the resins modified with oxamic acid show a superior affinity with other compounds and resins, so that they can make various kinds of composition having superior dispersing property. Therefore, by using the monomers containing an oxamic acid group and the resins modified with an oxamic acid as a hardening agent or an acid catalyser for an active hydrogen-containing resin or a resin of electrophilic character, and by using the the resins modified with oxamic acid as a hardening resin for various kinds of paints, they can make, for example, a paint film of a high anticorrosion property etc, where the oxamic acid group has disappeared after hardening.

DESCRIPTION OF THE INVENTION

Concrete examples of this invention are hereafter explained in combination with comparison examples in the following order.

① synthesis of the monomers containing an oxamic acid group

② polymerization of the monomers containing an oxamic acid group

③ synthesis of the compounds containing an oxamic acid group and transformed into high molecular weight compounds ④ synthesis of the resins modified with oxamic acid
⑤ compositions containing an oxamic acid group-containing compound
① Synthesis of the monomers containing an oxamic acid group

EXAMPLE 1

To 730.7 g (5 moles) of diethyl oxalate was added dropwise at room temperature a solution of 61.1 g (1 mole) of ethanolamine in 500 ml of acetone and, after the addition finished, treatment of the mixture by distillation under reduced pressure to remove the formed ethanol and the acetone and an excess amount of diethyl oxalate yielded ethyl 2-hydroxyethyloxamate. A mixture of 80.5 g (0.5 moles) of this ethyl 2-hydroxyethyloxamate, 50.6 g (0.5 moles) of triethylamine (hereinafter, referred to as TEA), 20.0 g of water, and 1000 ml of dioxane was warmed under reflux for 8 hours and treated with solvent removal followed by dehydration yielded a triethylamine salt of 2-hydroxyethyloxamic acid. A mixture of 11.7 g (0.05 moles) of this triethylamine salt of 2-hydroxyethyloxamic acid and 5.1 g (0.05 moles) of TEA was treated with dehydration by molecular sieve and then, dissolved with warming into 300 ml of THF. To this THF solution was added dropwise under a refluxing condition during 0.5 hours a solution of 5.2 g (0.05 moles) of methacrylic acid chloride in 30 ml of THF and, after the addition finished, the mixture was further stirred under the condition for 6 hours and treated with fractional extraction to get methacryloyloxyethyloxamic acid of the following structure:

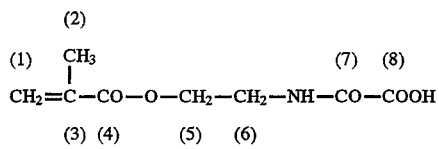

Besides, identification of the methacrylolyloxyethyloxamic acid 1 was carried out with $^{13}$C-NMR spectra analysis (ppm, in $CDCL_3$) and the results were 17.93 for (2), 38.86 for (6); 62.35 for (5), 120.59 for (1), 138.86 for (3), 158.01 for (7), 160.56 for (8), and 167.06 for (4).

EXAMPLE 2

In example 1, when the reaction of a triethylamine salt of 2-hydroxyethyloxamic acid with methacrylic acid chloride was performed, 5.5 g (0.05 moles) of methacryloylisocyanate were used instead of methacrylic acid chloride with no use of TEA and the reaction was carried out at room temperature. Except the forementioned, the same procedure as for example 1 was carried out to get methacryloylcarbamoyloxyethyloxamic acid of the following structure.

In example 1, when the reaction of a triethylamine salt of 2-hydroxyethyloxamic acid with methacrylic acid chloride was performed, 7.8 g (0.05 moles) of isocyanatethyl methacrylate were used instead of methacrylic acid chloride, TEA was not used, and 0.01 g of di-n-butyltin dilaurate (hereinafter, referred to as DBTL) was used as a reaction catalyst. Except the forementioned, the same procedure as for example 1 was carried out to get methacryloyloxyethyl carbamoyloxyethyloxamic acid.

EXAMPLE 4

In example 3, except that 10.1 g (0.05 moles) of m-isopropenyl-α, α-dimethylbenzylisocyanate was used instead of isocyanatethyl methacrylate, the same procedure as for example 3 was carried out to get [N'-(m-isopropenyl-α, α-dimethylbenzyl) carbamoyloxyethyl] oxamic acid of the following structure.

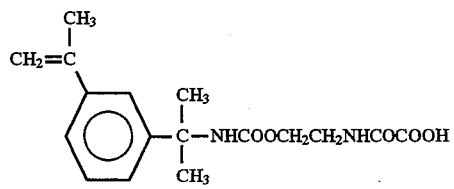

EXAMPLE 5

In example 1, except that 105.1 g (1.0 mole) of 2-(2-aminoethoxy)ethanol was used instead of ethanolamine, the same procedure as for example 1 was carried out to get methacryloyloxyethyl oxyethyloxamic acid of the following structure.

EXAMPLE 6

In example 2, except that 105.1 g (1.0 mole) of 2-(2-aminoethoxy)ethanol was used instead of ethanolamine, the same procedure as for example 2 was carried out to get methacryloylcarbamoy loxyethyloxyehyloxamic acid of the following structure.

EXAMPLE 7

In example 3, except that 105.1 g (1 mole) of 2-(2-aminoethoxy)ethanol was used instead of ethanolamine, the same procedure as for example 3 was carried out to get methacryloyloxyethyl carbamoyloxyethyloxyethyloxamic acid of the following structure.

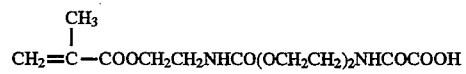

EXAMPLE 8

In example 4, except that 105.1 g (1.0 mole) of 2-(2-aminoethoxy)ethanol was used instead of ethanolamine, the same procedure as for example 4 was carried out to get [N'-(m-isopropenyl-α, α-dimethylbenzyl) carbamoyloxyethyloxyethyl] oxamic acid of the following structure.

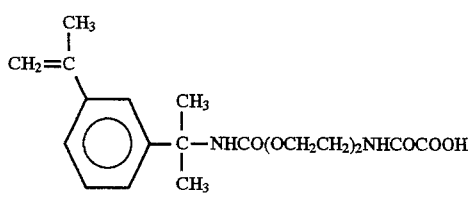

EXAMPLE 9

In a flask equipped with a stirrer, a thermometer, a dropping funnel, and a reflux condenser were placed 43 g (0.5 moles) of metacrylic acid and 300 ml of dichloromethane and to this mixture cooled with ice was added 103.5 g (0.5 moles) of dicyclohexylcarbodiimide during 15 minutes. After stirring for another 15 minutes, this mixture was added dropwise during 1 hour into a dichloroethane solution of 58 g of 1,6-hexamethylenediamine (0.5 moles, 50% by weight), and the reaction mixture obtained was warmed to 25° C. with stirring, filtrated to remove floating solid, and added into 300 ml of chilled water. Separation of an organic layer followed by distillation under reduced pressure to remove solvent yielded crystalline N-(6-aminohexyl)methacrylamide. A solution prepared by dissolving the crystals into 100 ml of ethanol was added dropwise during 2 hours maintaining the reaction temperature at 30° C. into 292 g (2 moles) of diethyl oxalate. After the addition finished, the stirring was continued at 25° C. for further 1 hour and then crystals separated were taken by filtration. The obtained crystals and 150 ml of water were placed in a flask, and hydrolysis was carried out with addition of 51 g (0.5 mole) of TEA into the aqueous solution during 30 minutes. To the resulting aqueous solution 41 ml of concentrated hydrochloric acid was added and then crystals separated was taken by filtration to obtain 6-methacryloylaminohexyloxamic acid 9.

Identification was carried out with IR, which showed absorptions for carboxylic acid at 1760 cm$^{-1}$, for carbonyl at 1680 cm$^{-1}$ and for amide at 1560 cm$^{-1}$. The acid value and molecular weight were, respectively, 215 (calcd. 223) and 252.

EXAMPLE 10

In a flask similar to that used for example 9 was placed 146 g (1.0 mole) of diethyl oxalate, and to this flask was added dropwise 26 g (0.25 moles) of diethanolamine maintaining reaction temperature at 30° C. during 1 hour. After the dropping finished, the stirring was continued at 25° C. for further 2 hours and then crystals separated were taken by filtration to obtain N-hydroxyethylmorpholine-2,3-dione.

Next, in a flask equipped with a stirrer, a thermometer, a decanter, a nitrogen gas-inlet tube, and a reflux condenser were placed 50 g (0.58 moles) of methacrylic acid, 0.1 g (0.1% by weight) of hydroquinone, and 200 ml of methyl isobutyl ketone (hereinafter, referred to as MIBK) and to this mixture was added 54 g (0.58 moles) of N-hydroxyethylmorpholine-2,3-dione, which was prepared in a way as above. Then, the mixture was warmed at 120° C. and the reaction continued for 2 hours by removing water being formed during the reaction by the decanter by means of azeotropic distillation. Return of the solution temperature to room temperature followed by removal of MIBK under reduced pressure gave 2-(1-morpholyl-2,3-dione)ethyl methacylate, which was placed with 120 ml of water in a flask and hydrolyzed by adding dropwise 59 g (0.58 moles) of TEA at 25° C. during 10 minutes to obtain a triethylammonium salt of (2-methacryloyloxyethyl)2-hydroxyethyoxamic acid 10.

This ammonium salt was completely soluble in water and identified by IR, which showed absorption bands at 1720 cm$^{-1}$ for an ester, 1610 cm$^{31}$ $^{1}$ for a carboxylic acid, and 2400–2800 cm$^{-1}$ for a triethylammonium salt, an acid value of 169 (calcd. 162), and a molecular weight of 332.

② Polymerization of monomers containing an oxamic acid group

EXAMPLE 11

Polymerization of the monomer containing an oxamic acid group 9 (synthesis of homopolymer)

In a flask similar to that used for example 9 were placed 30 ml of cellosolve acetate, being warmed at 100° C. To this flask were added dropwise 20 g (0.08 moles) of the monomer containing an oxamic acid group in the methacylamide series 9, obtained from said example 9, and 0.3 g of azobisisobutyronitrile (hereinafter, referred to as AIBN) during 3 hours. Then, further reaction was carried out for 1.5 hours maintaining the reaction temperature at 100° C. yielding an oxamic acid polymer in a methacrylamide series containing 40% of an unvolatile component. The polymer showed a water-soluble property by neutralizing with TEA.

EXAMPLE 12

Copolymerization of the monomer containing an oxamic acid group 9 (synthesis of copolymer)

A reaction similar to said example 11 was carried out with 20 ml of cellosolve acetate, 10.2 g (0.04 moles) of the monomer containing an oxamic acid group 9 obtained from said example 9, 3.8 g (0.04 moles) of methyl methacrylate, 5.8 g (0.05 moles) of n-butyl acrylate, and 0.9 g of AIBN to get an oxamic acid copolymer in a methacrylamide series containing 50% of an unvolatile component, which showed a water-soluble property by neutralizing with TEA.

EXAMPLE 13

Polymerization of the monomer containing an oxamic acid group 10 (synthesis of homopolymer)

A polymerization reaction was carried out in a way same to example 11 with 34.5 ml of cellosolve acetate, 23 g (0.1 mole) of 2-(1-morpholyl-2,3-dione)ethyl methacrylate obtained from said example 10, and 0.35 g of AIBN to get a morpholinedione polymer in a methacryl acid ester series containing 40% of unvolatile component. The polymer and 100 ml of water were placed in a flask and in a similar way as in said example 10, a hydrolysis reaction was carried out during 10 minutes at 25° C. with 10 g (0.1 mole) of TEA yielding a trimethylammonium salt of an oxamic acid polymer in a methacrylic acid ester series, wherein the acid polymer showed an acid value of 150 and a molecular weight of 4500 averaged by weight, and the trimethylammonium salt showed a water-dispersion property.

EXAMPLE 14

Copolymerization of the monomer containing an oxamic acid group 10 (synthesis of copolymer)

A reaction was carried out in a way similar to example 11 with 45 ml of cellosolve acetate, 6.8 g (0.03 moles) of 2-(1-morpholyl-2,3-dione)ethyl methacrylate obtained from said example 10, 10.0 g (0.1 mole) of methyl methacrylate, 15.4 g (0.12 moles) of n-butyl acrylate, 10.4 g (0.1 mole) of styrene, and 1.1 g of AIBN to obtain a morpholinedione copolymer in a methacrylic acid ester series containing 50% of an unvolatile component. To this solution were added 50 ml of water and 3 g (0.03 moles) of TEA to carry out a hydrolysis reaction and to get a triethylammonium salt of an oxamic acid copolymer in a methacrylic acid ester series, wherein the acid copolymer showed an acid value of 12 and a molecular weight of 8600 averaged by weight, and the triethylammonium salt was not soluble in water.

③ Synthesis of compounds containing an oxamic acid group and transformed into high molecular weight compound

EXAMPLE 15

Conversion of compounds containing an oxamic acid group into high molecular weight compounds In a flask similar to that used for said example 9 were placed 14.6 g (0.1 mole) of diethyl oxalate and to this was added at a time a 50% by weight solution of 11.6 g (0.1 mole) of 1,6 hexamethylenediamine in ethanol and the mixture was stirred until the reaction temperature came to room temperature and then, was allowed to react at room temperature for further 1 hour. After removal of ethanol under reduced pressure, the same procedure as used for example 9 gave a reaction product, which was treated with 5.1 g (0.05 moles) of TEA and subsequently, with 4.3 ml of concentrated hydrochloric acid to lead to an aimed, below-described polymer of the compound containing an oxamic acid group, which was identified as performed for example 9 by IR. An acid value of 32 and a molecular weight of 1753 averaged by weight were shown.

$$X-NH(CH_2)_6\text{+}NHCOCONH(CH_2)_6\text{+}_n NHCOCOOH$$

$$-X=-H \text{ or } -COCOOH$$

Chain-elongation reaction of polymer of the compound containing an oxamic acid group Into 17.5 g of dimethyl formamide were dissolved 17.5 g (0.01 mole) of said obtained polymer of the compound containing an oxamic acid group and to the solution obtained were added at a time 2.9 g (0.02 moles) of diethyl oxalate. The reaction mixture was stirred until the reaction temperature came to room temperature and allowed to react at room temperature for further 1 hour. After removal of dimethylformamide under reduced pressure, the reaction product obtained was treated with 1.0 g (0.01 mole) of TEA and subsequently, with 0.86 ml of concentrated hydrochloric acid in the same procedure as that for said example 9 to get an aimed chain-elongated polymer of the compound containing an oxamic acid group, which was as carried out for example 9 identified by IR and showed an acid value of 40 and a molecular weight of 2780 averaged by weight.

EXAMPLE 16

Conversion of modified epoxy resin into high molecular weight compound

In a flask equipped with a stirrer, a thermometer, a nitrogen-inlet tube, and a reflux condenser were placed 90 g of an epoxy resin (epoxy equivalent is 450) obtained from a reaction of bisphenol A with epichlorohydrin and then, added 60 g of MIBK to get a solution, which was warmed up to 120° C. under nitrogen atmosphere and to which was added 52 g of a ketimine material obtained from a reaction of diethylenetriamine with MIBK. The mixture was subjected to a reaction at 120° C. for 1.5 hours and, after the reaction finished, cooled, and hydrolysis of the ketimine was carried out with addition of 5.8 g of water to obtain an epoxy resin modified by an amine A.

Next, using a reaction apparatus similar to that used for said example 9, both compounds of 33 g (0.03 moles) of an amine-modified epoxy resin A, obtained in a way as above, and 4.4 g (0.03 moles) of diethyl oxalate were added at a time and allowed to react for 1 hour at room temperature. The reaction product obtained was treated with 2.0 g (0.02 moles) of TEA and subsequently, with 1.7 ml of concentrated hydrochloric acid in the same procedure as that for said example 9 to get an aimed epoxy resin polymer containing the below-described repeating structure unit:

$$-CHCH_2NCH_2CH_2NHCOCONHCH_2CH_2NCH_2CH-$$
$$\phantom{-CHCH_2NCH_2CH_2NHCOCONH}|$$
$$\phantom{-CHCH_2NCH_2CH_2NHCOCONHCH_2CH_2NCH}OH$$

Identification was carried out in the same way as for example 9 by IR and an acid value of 5 and a molecular weight of 11220 averaged by weight were indicated.

④ Synthesis of the resins modified with oxamic acid

EXAMPLE 17

Synthesis of epoxy resin (I) modified by oxamic acid

The reaction solution containing an amine-modified epoxy resin A, which was obtained after hydrolysis of the ketimine in said example 16, was added dropwise during 1 hour maintaining the reaction temperature at 30° C. to 58 g (0.4 moles) of diethyloxalate placed in another flask. After the dropping finished, stirring was further continued for 1 hour at 25° C. and then, under reduced pressure, MIBK was removed. Then, the thus-obtained reaction product and 300 ml of water were placed in a flask and a hydrolysis reaction was carried out by adding dropwise 23 g of TEA (0.22 moles) during 30 minutes. To this aqueous solution was added 23 ml of concentrated hydrochloric acid to perform reaction and an water-insoluble product formed was taken by decantation as a wanted product, that is an epoxy resin modified by oxamic acid (I) having the below-described structure moiety:

$$-CHCH_2N(CH_2CH_2NHCOCOOH)_2$$
$$\phantom{-CHCH_2N(CH_2CH}|$$
$$\phantom{-CHCH_2N(CH_2CH}OH$$

This modified resin (I) was neutralized with 50% TEA and, as a result, showed a water-soluble character. Identification was carried out with IR and NMR, where IR showed absorption bands at 1760 cm$^{-1}$ for a carboxylic acid, at 1680 cm$^{-1}$ for a carbonyl substituent and at 1560 cm$^{-1}$ for an amide and NMR signals appeared at 163.34 ppm and 166.17 ppm for a carbonyl carbon. There was shown an acid value of 171 (calcd. 160) and a molecular weight of 1392 averaged by weight.

EXAMPLE 18

Synthesis of epoxy resin modified with oxamic acid (II)

To 80 ml of MIBK were dissolved 150 g of the same epoxy resin as used for said example 16 in the same way and the solution was warmed up to 80° C. under nitrogen atmosphere. Then, to this solution were added dropwise during 10 minutes 35 g (0.33 moles) of diethanolamine. This reaction mixture was subjected to further reaction for 3 hours at 80° C. to obtain the modified epoxy resin B which has a primary hydroxyl group at a terminal carbon of the epoxy resin.

Separately, in another flask same as used for said example 9 were placed 148 g of isophoronediisocyanate (0.67 moles), 5.1 g of DBTL, and 65 ml of MIBK, and the mixture obtained was warmed up to 80° C. under nitrogen atmosphere, to which was added dropwise during 1 hour a solution of 106 g of N-hydroxyethylmorpholine-2,3-dione, which was obtained in the same procedure as that for example 10, in hot MIBK, and it was further subjected to reaction for 5 hours at 80° C. Then, into the MIBK solution of above-prepared modified epoxy resin B was added dropwise during 30 minutes at 80° C. said reaction solution of morpholine compound and the mixture thus-prepared was allowed to react for 2 hours at 100° C. and then, treated with distillation under reduced pressure to remove solvent and hydrolyzed with addition of 68 g (0.67 moles) of TEA and 2 liters of water to obtain a triethylammonium salt of the water-soluble epoxy resin modified with oxamic acid having the below-described modified structure moiety (II). Identification was carried out by IR, where showed absorption bands at 2400–2800 cm$^{-1}$ for a triethylammonium salt, 1700 cm$^{-1}$ for an urethane, and 1620 cm$^{-1}$ for a carboxylic acid. There were shown an acid value of 58 (calcd. 72) and a molecular weight of 3110 averaged by weight.

EXAMPLE 21

Synthesis of polyester resin modified with oxamic acid

A reaction apparatus similar to that for example 9 was used. In a flask were placed 105 g of a polyester resin, which showed a hydroxyl group value of 220 and a molecular weight of 2100, 91.4 g (0.41 moles) of isophoronediisocyanate, and 300 ml of acetone and, furthermore, added 1 g of DBTL and the mixture was allowed to react at 60° C. for 1 hour. The reaction product obtained was added dropwise to a mixture solution composed of 100 ml of acetone, 20 g of sulfuric acid, and 50 g of water during 30 minutes and, after addition, allowed to react for further 1 hour to obtain a solution of polyester resin modified with an amine, in which the amine moiety had a sulfuric acid salt form. Then, to this solution was added a mixture solution of 15.6 g of calcium hydroxide and 150 g of water and the mixture obtained was allowed to react at 60° C. for 2 hours and treated with solvent removal yielding 128 g of a polyester resin modified with an amine, which showed an amine value of 160 and had a molecular weight of 3700 averaged by weight. This resin was dissolved in 200 ml of ethanol and this solution was added dropwise in the way same as used for example 9 into a flask, where 292 g (2.0 moles) of diethyl oxalate were placed, and the mixture was allowed to react yielding an oxamic acid ester and then, treated with 37 g (0.37 moles) of TEA, water, and 30.8 ml of concentrated hydrochloric acid to get an aimed polyester resin modified with oxamic acid, which was identified by IR and had an acid value of 145.

EXAMPLE 22

Synthesis of polybutadiene resin modified with oxamic acid

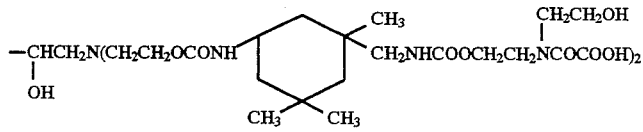

EXAMPLE 19

Synthesis of silicone resin modified with oxamic acid using an apparatus similar to that used for example 9, into a flask placed with 73 g (0.5 moles) of diethyl oxalate was added dropwise during 1.5 hours an ethanol solution of 380 g of silicone oil (KF 864 made from Sinetsu Silicone Co., LTD.) maintaining reaction temperature at 30° C. and then, the reaction mixture was stirred for 1 hour at 25° C. to get a resin modified with an oxamic acid ester. To this ester was added 30 ml of water and dropped 10.2 g (0.1 mol) of TEA during 30 minutes to carry out a hydrolysis reaction. The aqueous solution thus-obtained was treated with 8.3 ml of concentrated hydrochloric acid getting a wanted silicone resin modified with oxamic acid. Identification was carried out in the same way as described in example 9. The acid value was 10.

EXAMPLE 20

Synthesis of amino resin modified with oxamic acid

In a similar way as used for said example 19, a reaction of 146 g (1.0 mole) of diethyl oxalate with 89 g of a melamine resin (J-820-60 produced from Dainippon Inki Kagaku Kogyo Co., Ltd., molecular weight of 1960) was carried out to get a resin modified with an oxamic acid ester, which was treated with 20.4 g (0.2 moles) of TEA, water, and 16.6 ml of concentrated hydrochloric acid to obtain an aimed amino resin modified with oxamic acid. Identification was carried out by IR and the acid value was 134.

In the same way as for said example 19, a reaction was carried out between 73 g (0.5 moles) of diethyl oxalate and 30 g of a polybutadiene resin modified with an amine, which had an amine value of 187 and a molecular weight of 1200, to obtain a resin modified with an oxamic acid ester, which was treated with 10.2 g (0.1 mole) of TEA, water, and 8.3 g of concentrated hydrochloric acid leading to an aimed polybutadiene resin modified with oxamic acid, that was identified by IR and had an acid value of 180.

EXAMPLE 23

Synthesis of polyethyleneimine resin modified with oxamic acid

In the same way as for said example 19, a reaction was carried out between 73 g (0.5 moles) of diethyl oxalate and 40 g of polyethyleneimine resin (EPOMIN P-1000 produced from Nippon Shokubai Kagaku Kogyo Co., Ltd. and molecular weight of 70,000) to obtain a resin modified with an oxamic acid ester, which was treated with 20.4 g (0.2 moles) of TEA, water, and 16.6 ml of concentrated hydrochloric acid to obtain an aimed polyethyleneimine resin modified with oxamic acid, that was identified by IR and had an acid value of 275.

EXAMPLE 24

Synthesis of polyamide resin modified with oxamic acid

In the same way as for said example 19, a reaction was carried out between 173 g (1.2 moles) of diethyl oxalate and 90 g of a polyamide resin (molecular weight of 4500) to obtain a resin modified with an oxamic acid ester, which was similarly treated with 5.1 g (0.05 moles) of TEA, water, and 3.5 ml of concentrated hydrochloric acid to obtain an aimed polyamide resin modified with oxamic acid, that was identified by IR and had an acid value of 30.

EXAMPLE 25

Synthesis of fluororesin modified with oxamic acid

Except that 60 g of a fluororesin modified with acrylamide (molecular weight 2,000) was used instead of the polyamide resin, the procedure same as used for example 24 gave an aimed fluororesin modified with oxamic acid, that was identified by IR and had an acid value of 40).

⑤ Compositions containing an oxamic acid group-containing compound

EXAMPLE 26

Application of water-soluble resin for thermally hardening reaction (1)

The epoxy resin modified with oxamic acid (I), 10 g, obtained from said example 17, 6.3 g of blockisocyanate prepared from 3 mole equivalents of trilenediisocyanate and 1 mole equivalent of trimethylolpropane, and 1.5 g of TEA were dissolved into 18 ml of water. This solution was applied on a tinplate and warmed at 190° C. for 30 minutes to get a film having a thickness of 20 μm. A part of this film was taken for IR measurement, where the carboxylic acid absorption at about 1760 $cm^{-1}$ and the carbonyl absorption at about 1680 $cm^{-1}$ observed before heating disappeared and, instead, a new absorption was observed at 1630 $cm^{-1}$ assignable for a formamide group. This result indicates that the oxamic acid, that is an ionic group, disappeared from the film after the thermal treatment.

EXAMPLE 27

Application of water-soluble resin for thermally hardening reaction

Blockisocyanate, 9.8 g, same to that used for said example 26, and 20 g of the epoxy resin modified with oxamic acid (II) obtained from said example 18 were dissolved into 20 ml of water and the procedure same as for example 26 gave a film having a thickness of 20 μm. A part of the film was taken for IR measurement, where the carboxylic acid absorption at about 1620 $cm^{-1}$ observed before heating disappeared and a new absorption was observed at 1660 $cm^{-1}$ assignable for a formamide group. This result indicates that the oxamic acid, that is an ionic group, disappeared from the film after the thermal treatment.

EXAMPLE 28

Hardening reaction at low temperature with polyamine

A mixture of 15 g of an oxamic acid copolymer in a methacrylamide series, obtained from said example 12, and 2.1 g of diethylenetriamine was applied on a tinplate and warmed for 20 minutes at 50° C. to get a film having a thickness of 20 μm. A pencil hardness examination for this film was carried out and the result indicates formation of a strong, solid film of pencil hardness H.

EXAMPLE 29

Application for resin composition of an organic solvent form

A resin composition of an organic solvent form was obtained by dissolving into 40 parts of an organic solvent (N,N-dimethylformamide) 30 parts of an epoxy resin polymer modified with oxamic acid, which was obtained from said example 16 and had a molecular weight of 11220 and an acid value of 5, and 10 parts of a methylated and butylated melamine resin (Nikarakku MX 40 made from Nippon Carbide Kogyo Co., LTD).

Said composition was applied for a plate treated with zinc phosphate so as to make a film of thickness 20 μm. A hardened film (pencil hardness of 2H) was obtained by baking it at 150° C. for 30 minutes. Water-resistant and anticorrosion properties for this film was examined. The water-resistant property was evaluated by examining presence or absence of chalking and swelling for a film treated with soaking in water of 50° C. for 48 hours. The anticorrosion property was evaluated by examining exfoliated width due to a tape exfoliation from a cutting part after a salt spray examination was carried out for 150 hours. The results indicate that there is no chalking and swelling for the film after soaking in warm water for 48 hours and that the exfliated width due to tape exfliation was 3 mm after salt-spray examination during 150 hours.

Accordingly, it was found that the film obtained has a sufficient crosslinking density and superior water-resistant and anticorrosion properties.

EXAMPLE 30

Use as an electrodeposition coating resin

In a flask equipped with a stirrer, a thermometer, a dropping funnel, and a reflux condenser were placed 50 g of the epoxy resin modified with oxamic acid (I), obtained from said example 17, 31.5 g of blockisocyanate as a hardening agent which was similar to example 26, 0.1 g of dibutyltinoxide, and 7.5 g of TEA, and to this mixture was added dropwise 504 g of water during 1 hour at 80° C. to get a resin-dispersed solution for electrodeposition coating. This resin-dispersed solution did not show, after standing for 1 month at room temperature, abnormalities such as viscosity increase and separation and also, still had superior dispersion stability.

Next, said resin-dispersed solution was placed in a stainless steel beaker (an anode) and, using as a cathode a test pannel plate (a cold rolling steel plate) deoiled with xylene, an electrodeposition experiment was carried out with 100 voltage and, as a result, a water-insoluble product was separated out on the cathode.

Furthermore, the separated resin was heated for hardening for 30 minutes at 190° C. to obtain an uniformly electrodeposited film having a thickness of 25 μm. The pencil hardness for this film was 2H and the results from capacity experiments carried out similarly to the case of said example 29 showed superior water-resistant, anticorrosion, and solvent-resisting properties.

Use as a hardening agent for an epoxy resin

EXAMPLE 31

As an electrophilic resin, was used 9.3 g of an epoxy resin, obtained from a reaction between bisphenol A was dissolved in 15 g of MIBK with a 40% solution of 32 g of a homopolymer of the monomer containing an oxamic acid group 9, obtained from example 11, in cellosolve acetate. This solution was applied on a tinplate and warmed at 140° C. for 3 hours to get a paint film of thickness 20 μm. The results obtained from a pencil hardness examination for the paint film confirmed formation of a strong film of pencil hardness 2H.

Thus, it was confirmed that a polymer of a monomer containing an oxamic acid group can be used as a hardening agent for an electrophilic resin.

EXAMPLE 32

Application as an acid-catalyst for resin hardening

To a clear lacquer for finishing for metallics composed of 30 weight parts (hereinafter, referred to as ⌈part⌋) of an acryl resin of a thermally hardening type (molecular weight of 8000, an acid value of 10, hydroxl group value of 80), 10 parts of methylated and butylated melamine resin (same as for example 29), and 60 parts of an organic solvent (a mixture solution of xylene and isobutyl alcohol) was added a 40% cellosolve solution of 1.5 parts of a homopolymer ammonium salt of the monomer containing an oxamic acid group 9, obtained from example 11, to get a resin composition of an organic solvent type.

The composition was applied on an iron plate treated with zinc phosphate to make a film of thickness 20 μm and baked at 150° C. for 30 minutes to form a hardened paint film.

The pencil hardness and the water-resistant and anticorrosion properties for this paint film obtained were evaluated as for said example 29.

COMPARISON EXAMPLE

In example 32, except that 0.5 parts of an acid hardening catalyst of an ammonium salt type of dodecylbenzenesulfonic acid was used instead of an oxamic acid derivative, a similar procedure gave a resin composition of an organic solvent type.

Furthermore, in a similar way as the above, a paint film was formed from the composition, and property examination was similarly carried out for the film. Results obtained are shown in table 1.

TABLE 1

|  | Example 32 | Comparison Example |
| --- | --- | --- |
| Pencil hardness | 2H | 2H |
| After soaking in warm water | no change | delustering observed |
| Tape-exfoliated width | 2 mm | 6 mm |

As seen in table 1, it was observed that the paint film, where the oxamic acid derivatives were used as an acid hardening catalyst, has sufficient crosslinking density and superior water-resistant and anticorrosion properties. In contrast, regarding the paint film in comparison example, although chalking and swelling were not observed in the film after treatment with soaking in warm water, delustering was found and the exfoliated width due to tape exfoliation after treatment with salt-spraying was so big as 6 mm and, therefore, it was clarified that, although the paint film was sufficiently crosslinked, the water-resistant and anticorrosion properties were lowered due to the fact that the acid catalyst was remaining in the paint film.

What is claimed is:

1. A compound containing an oxamic acid group denoted by the following general formula (II):

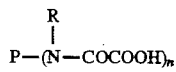

in which P is a residue of a high molecular weight compound having a molecular weight of 1,000 or more, R is a hydrogen atom, an alkyl group of from 1 to 5 carbon atoms, or a benzyl group, and n is a positive integral number, R may have a hydroxyl group as a substituent.

2. A compound as claimed in claim 1, wherein P is a resin residue selected from the group consisting of an acryl resin, a polyester resin, a polyamide resin, an epoxy resin, an amino resin, a polyethyleneimine resin, a resin in a hydrocarbon series, a silicone resin, a fluororesin, and resins modified from those.

3. A hardening resin composition containing a compound as claimed in claim 1 which contains two or more oxamic acid groups in the molecule, and a compound which shows mutual reactivity with the oxamic acid group.

4. A composition as claimed in claim 3, wherein the compound containing an oxamic acid group involves a resin residue selected from the group consisting of an acryl resin, a polyester resin, an epoxy resin, a polyamide resin, and an amino resin.

5. A composition as claimed in claim 3, wherein the compound showing mutual reactivity with an oxamic acid group involves at least one group selected from the group consisting of a hydroxyl group, an amino group, and an epoxy group.

6. A resin composition containing at least a compound as claimed in claim 1, a basic compound, and water.

7. A composition as claimed in claim 6, wherein the compound containing an oxamic acid group involves a resin residue selected from the group consisting of an acryl resin, a polyester resin, a polyamide resin, an epoxy resin, an amino resin, a polyethyleneimine resin, a silicone resin, a fluororesin, and a resin in a butadiene series.

8. A composition as claimed in claim 6, wherein the basic compound is an amine compound.

9. A surface-active agent which is composed of a compound containing an oxamic acid group as claimed in claim 1.

10. A surface-active agent as claimed in claim 9, wherein the compound containing an oxamic acid group involves a resin residue selected from the group consisting of a resin in a hydrocarbon series, a fluororesin, and a silicone resin.

11. A compound containing an oxamic group of the formula (I)

in which A represents a group of radical polymerization character, said group containing a C=C double bond to which a carbonyl group or a phenylene group is attached to a carbon atom thereof; Y is an alkylene group of from 1 to 8 carbon atoms in which a portion of the carbon atoms in Y may be replaced by an oxygen atom; and R is a hydrogen atom, an alkyl group of from 1 to 5 carbon atoms or a benzyl group, which R may contain a hydroxy group as a substituent thereof.

12. A compound as claimed in claim 11, wherein the group A of the formula (I) is selected from a group consisting of the following formulas (A-1), (A-2), (A-3), (A-4), and (A-5):

-continued

(A-3)

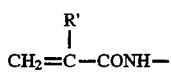
(A-4)

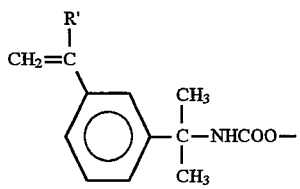
(A-5)

in which R' is a hydrogen atom or a methyl group.

13. A compound as claimed in claim 11, said R is a hydroxyethyl group.

14. A process for producing a compound as claimed in claim 13, comprising the steps of:
    adding a necessary amount of water in presence of an amine compound to a substituted morpholinedione containing one or more of the below-described morpholine-2,3-dione group intramolecularly, wherein said morpholinedione is hydrolyzed with ring-cleavage of the morpholinedione group to get an ammonium salt; and neutralizing said ammonium salt with an acid.

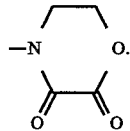

15. A compound as claimed in claim 13, having the formula

* * * * *